(12) United States Patent
Bruce (10) Patent No.: US 6,730,073 B2
(45) Date of Patent: May 4, 2004

(54) METHOD OF PERFORMING A LASIK PROCEDURE AND TONOMETER SYSTEM FOR USE THEREWITH

(75) Inventor: John C. Bruce, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 26 days.

(21) Appl. No.: 09/867,041

(22) Filed: May 29, 2001

(65) Prior Publication Data

US 2002/0049428 A1 Apr. 25, 2002

Related U.S. Application Data

(60) Provisional application No. 60/242,337, filed on Oct. 20, 2000.

(51) Int. Cl.$^7$ ............................................... A61B 18/18
(52) U.S. Cl. ............................... 606/4; 606/5; 128/898; 600/398
(58) Field of Search ................... 606/4–6, 10; 128/898; 600/398, 399, 405; 351/200, 202

(56) References Cited

U.S. PATENT DOCUMENTS

| | | | |
|---|---|---|---|
| 4,860,755 A | 8/1989 | Erath | |
| 5,165,409 A | 11/1992 | Coan | |
| 5,671,737 A * | 9/1997 | Harosi | 128/645 |
| 5,857,969 A | 1/1999 | Massey et al. | 600/398 |
| 6,113,542 A | 9/2000 | Hyman et al. | 600/398 |
| 6,213,943 B1 * | 4/2001 | Abreu | 600/405 |
| 6,247,473 B1 * | 6/2001 | Yavitz | 128/898 |

FOREIGN PATENT DOCUMENTS

| | | | |
|---|---|---|---|
| EP | 0 315 329 A2 | 10/1988 | A61B/3/16 |
| EP | 1 027 873 A | 8/2000 | A61F/9/013 |
| WO | WO 02/45634 A2 | 6/2002 | |

OTHER PUBLICATIONS

Medtronic Solan Instruction Manual; "Model 30 Classic™ Pneumatonometer" pp. 1–31; ©2000.

* cited by examiner

Primary Examiner—Linda C. M. Dvorak
Assistant Examiner—Ahmed M Farah
(74) Attorney, Agent, or Firm—Timothy A. Czaja; Trevor D. Arnold (57) ABSTRACT

A method of performing a LASIK procedure. The method includes providing LASIK instrumentation, preferably including an automated microkeratome instrument and an excimer laser. The microkeratome device includes both a microkeratome as well as a suction ring. A high-pressure range tonometer instrument is also provided. The tonometer includes a probe for sensing a parameter of the eye indicative of intraocular pressure, and is capable of providing intraocular pressure measurements in excess of 80 mm Hg; more preferably in excess of 100 mm Hg; most preferably up to or in excess of 120 mm Hg. The suction ring is positioned over the patient's eye, and a vacuum applied. The high-pressure range tonometer probe is positioned relative to the eye so as to sense a parameter indicative of intraocular pressure. The measured intraocular pressure is then provided to the surgeon. Based upon the measured intraocular pressure, the surgeon determines whether the corneal site is properly prepared for optimal microkeratome incision. For example, the surgeon determines whether the measured intraocular pressure meets or exceeds a minimum value. In one preferred embodiment, the intraocular pressure must be equal to or exceed 100 mm Hg, although other minimum values, such as 110 mm Hg, 120 mm Hg, etc. are equally acceptable. Once sufficient intraocular pressure has been established, the LASIK procedure proceeds in accordance with accepted protocol. For example, the microkeratome is employed to cut a flap in the cornea which is then folded back. The excimer laser ablates the exposed portion of the cornea to effectuate the desired vision correction. Finally, the flap is replaced and the surgery is complete.

27 Claims, 3 Drawing Sheets

METHOD OF PERFORMING A LASIK PROCEDURE AND TONOMETER SYSTEM FOR USE THEREWITH

CROSS-REFERENCE TO RELATED APPLICATIONS

This application claims the benefit of U.S. Provisional Application No. 60/242,337, filed on Oct. 20, 2000.

BACKGROUND OF THE INVENTION

The present invention relates to an improved laser-assisted intrastromal in-situ keratomileusis ("LASIK") procedure. More particularly, it relates to a LASIK procedure in which intraocular pressure is measured prior to cutting a flap in the cornea, along with a tonometer system capable of providing elevated intraocular pressure readings.

LASIK procedures have recently become highly popular for correcting various vision problems such as myopia, astigmatism, and hyperopia. In general terms, an automated microkeratome is employed to cut a large, superficial flap in the cornea. The flap is typically 160–180 microns in depth so as to include the first two corneal layers (i.e., the epithelium and Bowmans layer), while leaving the third layer or stroma in tact. The arc length of the so-defined flap is typically on the order of 300°, such that the flap can be folded back to expose the stroma. An excimer laser is then used to ablate or reshape the corneal stroma to effectuate the desired vision correction or enhancement. To this end, the excimer laser is typically centered on the prepupillary area. Following ablation, the flap is replaced or folded back. After a few minutes, the flap remains in place without requiring sutures, much like a suction cup.

As with other popular surgical procedures, numerous efforts have been made to improve the microkeratome and excimer laser instruments. One distinct aspect of the LASIK procedure, however, remains relatively rudimentary. In particular, to properly form the desired flap, the eyeball is subjected to a vacuum prior to cutting with the microkeratome. To this end, the microkeratome device includes a suction ring placed about the eye for applying the vacuum, resulting in a greatly elevated intraocular pressure as well as a slight distension of the eyeball from the socket. The elevated intraocular pressure renders the eyeball rigid, thereby promoting uniform, properly-sized incision by the microkeratome. Conversely, inadequate intraocular pressure can undesirably result in a thin, irregular flap.

As a point of reference, normal intraocular pressure is approximately 15–20 mm Hg. During a LASIK procedure, however, the intraocular pressure is preferably raised to a level in excess of 80 mm Hg to ensure proper eyeball rigidity. The optimal intraocular pressure for uniform microkeratome incision is currently unknown, due to the fact that available intraocular pressure sensing devices (or tonometers) have an upper limit at or below 80 mm Hg, as described in greater detail below. Thus, the currently accepted technique of evaluating intraocular pressure prior to microkeratome flap formation is known as a "finger" or "digit" method, whereby the surgeon touches the patient's eye with his/her finger and speculates as to the intraocular pressure. Obviously, evaluating intraocular pressure with the finger is highly subjective as the surgeon is required to guess as to whether the eye "feels" sufficiently rigid.

As indicated above, various tonometry instruments do exist for measuring intraocular pressure. Generally, there are two types of tonometers, including applanation and indentation. Either approach requires numbing of the eye and entails applying a force, via a probe placed against the cornea, that produces a distortion of the eyeball globe. The pressure required to applanate or indent the cornea is indicative of the intraocular pressure.

The most popular form of indentation tonometer is known as a Schiotz tonometer. With the Schiotz tonometer, a plunger produces a corneal indentation, the depth and volume of which are dependent upon the intraocular pressure. Other indentation tonometers, such as a Wolfe tonometer, rely on similar principals but with different internal or probe components, such as a calibrated spring.

An applanation tonometer measures the force required to flatten a certain area of the cornea. Examples of applanation tonometers include Goldmann tonometer, Draeger applanation tonometer, Mackay-Marg tonometer, and pneumatonometer, to name but a few. The Goldmann tonometer was the first example of a variable force applanation tonometer, and is still considered to be highly reliable. Other devices, such as the Mackay-Marg tonometer, measure intraocular pressure by analyzing deflections in membranes or crystals when the device is pressed against the eye. A pneumatonometer probe contains a gas and employs a pressure sensor or transducer. The pneumatonometer determines intraocular pressure by bringing a small burst of air toward the cornea. A backpressure is sensed, and is proportional to the intraocular pressure.

A third tonometry technique is generally referred to as "non-contact" and uses a stream of air (or "puff") to flatten a portion of the cornea, while a light source is reflected off of that flattened portion. The pressure or force required to cause the sensed displacement is indicative of the intraocular pressure. While non-contact tonometers do not require anesthetizing the eye prior to use, they are generally regarded as being less accurate than applanation or indentation tonometers.

Each of the above-described tonometer systems were developed to detect the onset of glaucoma. Glaucoma is typically characterized by an increased intraocular pressure, above the normal 20 mm Hg. In this regard, a patient exhibiting a sensed intraocular pressure in excess of 30 mm Hg is typically deemed to be at risk for glaucoma; a 40–50 mm Hg intraocular pressure is highly abnormal, resulting in immediate emergency treatment. With these general parameters in mind, then, virtually all available tonometer devices have a maximum reading of approximately 50 mm Hg. In other words, for glaucoma testing, there is no need to provide for a larger range. Further, by limiting the range to approximately 50 mm Hg, the overall accuracy of the device can be increased.

At least one currently available pneumatonometer is able to accurately measure pressure up to 80 mm Hg. In particular, the Model 30 Classic™ pneumatonometer, available from Medtronic-Solan (formerly Mentor Ophthalmics) of Jacksonville, Fla., provides an intraocular pressure measurement in the range of 5–80 mm Hg. The Model 30 Classic™ device provides this enhanced intraocular pressure range to perform not only tonometer functions, but also tonography (i.e., evaluation of aqueous outflow of the eye). The accuracy of the Model 30 Classic™ is +/−2 mm Hg, and therefore is highly satisfactory for tonometery applications. It is believed that one other available tonometer has an upper limit of 90 mm Hg, but is limited to a simple "go or no-go" indication for intraocular pressure in excess of 50 mm Hg. Beyond these two examples, no device exists for measuring intraocular pressures in excess of 50 mm Hg.

The microkeratome and excimer laser instruments used for LASIK procedures continue to improve. However, the "finger touch" technique of evaluating intraocular pressure prior to microkeratome incision presents a distinct opportunity for complications. Therefore, a need exists for an improved LASIK procedure that promotes optimal flap formation and a tonometry system for effectuating this procedure.

SUMMARY OF THE INVENTION

One aspect of the present invention relates to a method of performing a LASIK procedure. The method includes providing LASIK instrumentation, preferably including an automated microkeratome instrument and an excimer laser. The microkeratome device includes both a microkeratome as well as a suction ring. A high-pressure range tonometer instrument is also provided. The tonometer includes a probe for sensing a parameter indicative of intraocular pressure, and is capable of providing intraocular pressure measurements in excess of 80 mm Hg; more preferably in excess of 100 mm Hg; most preferably up to or in excess of 120 mm Hg.

With these components in hand, the microkeratome instrument is positioned relative to the patient, including applying the suction ring over the patient's eye. A vacuum pressure is then applied to the eye via the suction ring. The high-pressure range tonometer probe is positioned relative to the eye so as to sense a parameter indicative of intraocular pressure. The measured intraocular pressure is then provided to the surgeon. Based upon the measured intraocular pressure, the surgeon determines whether the corneal site is properly prepared for optimal microkeratome incision. For example, the surgeon determines whether the measured intraocular pressure meets or exceeds a minimum value. In one preferred embodiment, the intraocular pressure must be equal to or exceed 100 mm Hg, although other minimum values, such as 110 mm Hg, 120 mm Hg, etc. are equally acceptable. Once sufficient intraocular pressure has been established, the LASIK procedure proceeds in accordance with accepted protocol. For example, the microkeratome is employed to cut a flap in the cornea that is then folded back. The excimer laser is used to ablate the exposed portion of the cornea to effectuate the desired vision correction. Finally, the flap is replaced and the surgery is complete. In one preferred embodiment, an existing pneumatonometer is reconfigured to provide intraocular pressure measurements up to, or in excess of, 120 mm Hg for use with the above-described method.

Another aspect of the present invention relates to a method of measuring an intraocular pressure in excess of 80 mm Hg as part of LASIK procedure. The method includes providing a tonometer having a maximum intraocular pressure measuring capability of less than 80 mm Hg. A vacuum pressure is then applied to a patient's eye. A range setting is established for the tonometer. Following application of the vacuum, an initial intraocular pressure measurement for the eye is received from the tonometer. A corrected intraocular pressure measurement is then determined based upon the initial intraocular pressure measurement in the range setting. Finally, the corrected intraocular pressure measurement is displayed. With this methodology, a corrected intraocular pressure measurement of greater than 80 mm Hg can be measured and displayed. In one preferred embodiment, the range setting of the tonometer is established as being either "low" or "high". In an even more preferred embodiment, when the tonometer is designated as operating in the high range, a factor of 40 mm Hg is added to the initial intraocular pressure measurement.

Yet another aspect of the present invention relates to a system for measuring an intraocular pressure in excess of 80 mm Hg for patient's eye undergoing an LASIK procedure. The system includes a tonometer and a processor. The tonometer is capable of measuring a maximum intraocular pressure of less than 80 mm Hg. The processor is associated with the tonometer for receiving intraocular pressure measurements from the tonometer. Further, the processor is capable of establishing a range setting for the tonometer. The processor is further capable of receiving an initial intraocular pressure measurement from the tonometer and determining a corrected intraocular pressure measurement based upon the initial intraocular measurement and the range setting. Finally, the processor is capable of displaying the corrected intraocular pressure measurement. With the system of the present invention, an intraocular pressure of greater than 80 mm Hg can be provided via a tonometer having limited pressure applications. Thus, the system is highly useful with LASIK procedures.

DESCRIPTION OF THE PREFERRED EMBODIMENTS

Figure 1:
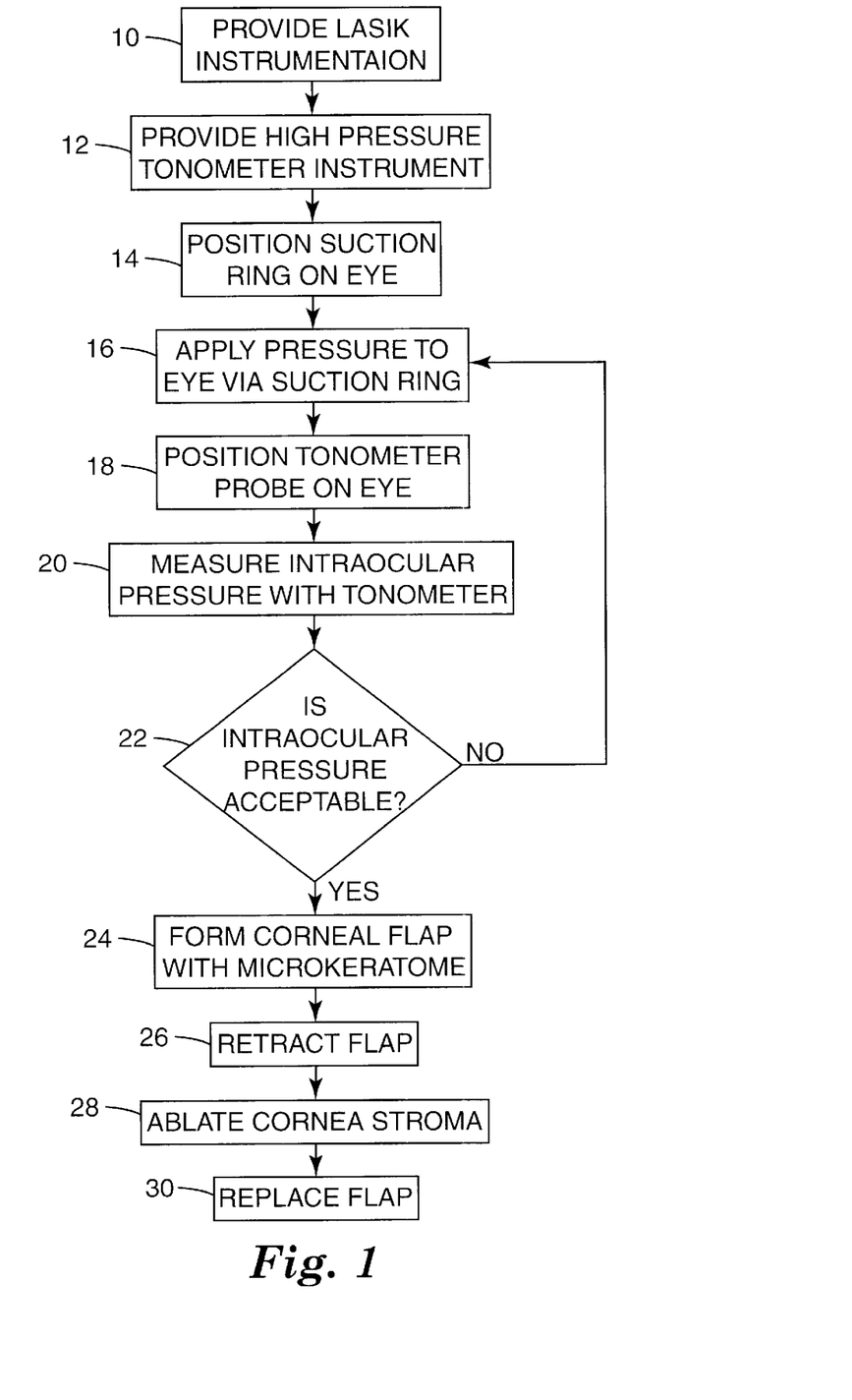
FIG. 1 is a flow diagram illustrating a LASIK procedure in accordance with the present invention.

One preferred LASIK procedure methodology in accordance with the present invention is illustrated by the flow diagram of FIG. 1. As a point of reference, the LASIK procedure of the present invention is similar in many respects to current protocol. Further, prior to initiation of the LASIK procedure, it is assumed that the surgeon has evaluated the patient and determined the appropriateness of the LASIK procedure for effectuating vision correction.

At step 10, LASIK instrumentation is provided. The LASIK instrumentation is of a type commonly known in the art and typically includes an automated microkeratome and an excimer laser. The instruments can assume a wide variety of forms known in the art, for example an automated microkeratome system sold under the tradename Automated Corneal Shaper by Chiron of Clairemont, Calif., that includes both a microkeratome as well as a suction ring. Similarly, excimer lasers useful for LASIK applications are well known, available, for example, from Autonomous Technologies, Chiron Technolos, VISX, etc. Other available LASIK instruments are equally acceptable.

At step 12, a high-pressure range tonometer instrument is provided. As described in greater detail below, the tonometer can assume a wide variety of forms, but includes a probe and is preferably a pneumatonometer. Regardless of the exact form, the high-pressure range tonometer is preferably configured to measure intraocular pressures in excess of 80 mm Hg; more preferably in excess of 100 mm Hg.; most preferably up to or in excess of 120 mm Hg. Further, the so-provided tonometer is preferably highly accurate at elevated intraocular pressures, exhibiting an accuracy of +/−2 mm Hg.

At step 14, after applying an anesthetic to the eye, the microkeratome system is properly positioned relative to the patient. In particular, the suction ring is applied to the patient's eye in accordance with accepted procedures.

At step 16, a pressure is applied to the eye via the suction ring. This applied pressure renders the eye more rigid by greatly elevating the intraocular pressure. The unique characteristics of an individual eye render it impossible to precisely quantify an optimal vacuum level provided by the suction ring. Instead, as with current LASIK techniques, the surgeon initiates the vacuum at the suction ring to a generally accepted level, and proceeds to step 18.

At step 18, the high-pressure range tonometer is properly positioned relative to the eye. In particular, the probe portion of the tonometer is placed in contact with the patient's eye (e.g., cornea or sclera).

With the probe properly positioned, the surgeon is provided with an intraocular pressure measurement via the high-pressure range tonometer at step 20. This is in direct contrast to currently employed LASIK techniques whereby the surgeon "evaluates" eye rigidity by simply touching the cornea with his or her finger. By employing a high-pressure range tonometer, the surgeon obtains an accurate measurement of intraocular pressure.

At step 22, the surgeon determines whether the so-measured intraocular pressure is sufficient for microkeratome incision. In one preferred embodiment, an intraocular pressure reading in excess of 80 mm Hg is deemed acceptable. Alternatively, other minimum intraocular pressures, such as 100 MM Hg, 110 mm Hg, 120 mm Hg, etc., can be employed. Regardless, by employing a high-pressure range tonometer, the method of the present invention affords the surgeon to accurately determine intraocular pressure, and thus make a consistent determination as to whether the corneal site is properly prepared for optimal microkeratome incision. While the decision of whether the measured intraocular pressure is sufficient to proceed is preferably left to the surgeon, in an alternative embodiment, a processing device is associated with the high pressure tonometer that performs this evaluation automatically based upon previously entered parameters.

If the surgeon determines that the measured intraocular pressure is below the acceptable value ("no" at step 22), the procedure returns to step 16 whereby additional pressure is applied to the eye via the suction ring. If, after several attempts to achieve an acceptable intraocular pressure are unsuccessful, the procedure can be terminated.

Alternatively, where the measured intraocular pressure does meet or exceed the acceptable value ("yes" at step 22), the procedure continues to step 24 whereby the microkeratome cuts a large, superficial flap in the cornea. Formation of the flap via the microkeratome blade is well known in the art, and typically starts from the temporal side and stops nasally before a complete circle has been cut. As previously described, the flap typically has a thickness of 140–160 micrometers, and an arc length of 300°. Alternatively, a wide variety of other flap configurations, cutting techniques, etc. are equally acceptable. By ensuring that the intraocular pressure meets or exceeds the minimum value set forth at step 22, formation of a uniform, properly sized flap by the microkeratome at step 24 is promoted.

Following flap formation, the LASIK procedure of the present invention proceeds identical to accepted protocol. For example, at step 26, the flap is retracted. At step 28, the excimer laser is centered on the prepupillary area, and a multi-zone ablation is performed to effectuate the desired vision correction. At step 30, the flap is replaced or repositioned, and the surgery is complete.

The LASIK procedure of the present invention provides a marked improvement over current techniques whereby intraocular pressure is both accurately measured and evaluated prior to microkeratome incision. The current, subjective technique of manually assessing eye rigidity with the surgeon's finger is eliminated. Similarly, by utilizing an actual intraocular pressure measurement, the method of the present invention affords the surgeon with a positive determination of whether the corneal environment is properly prepared for optimal microkeratome incision.

Figure 2:
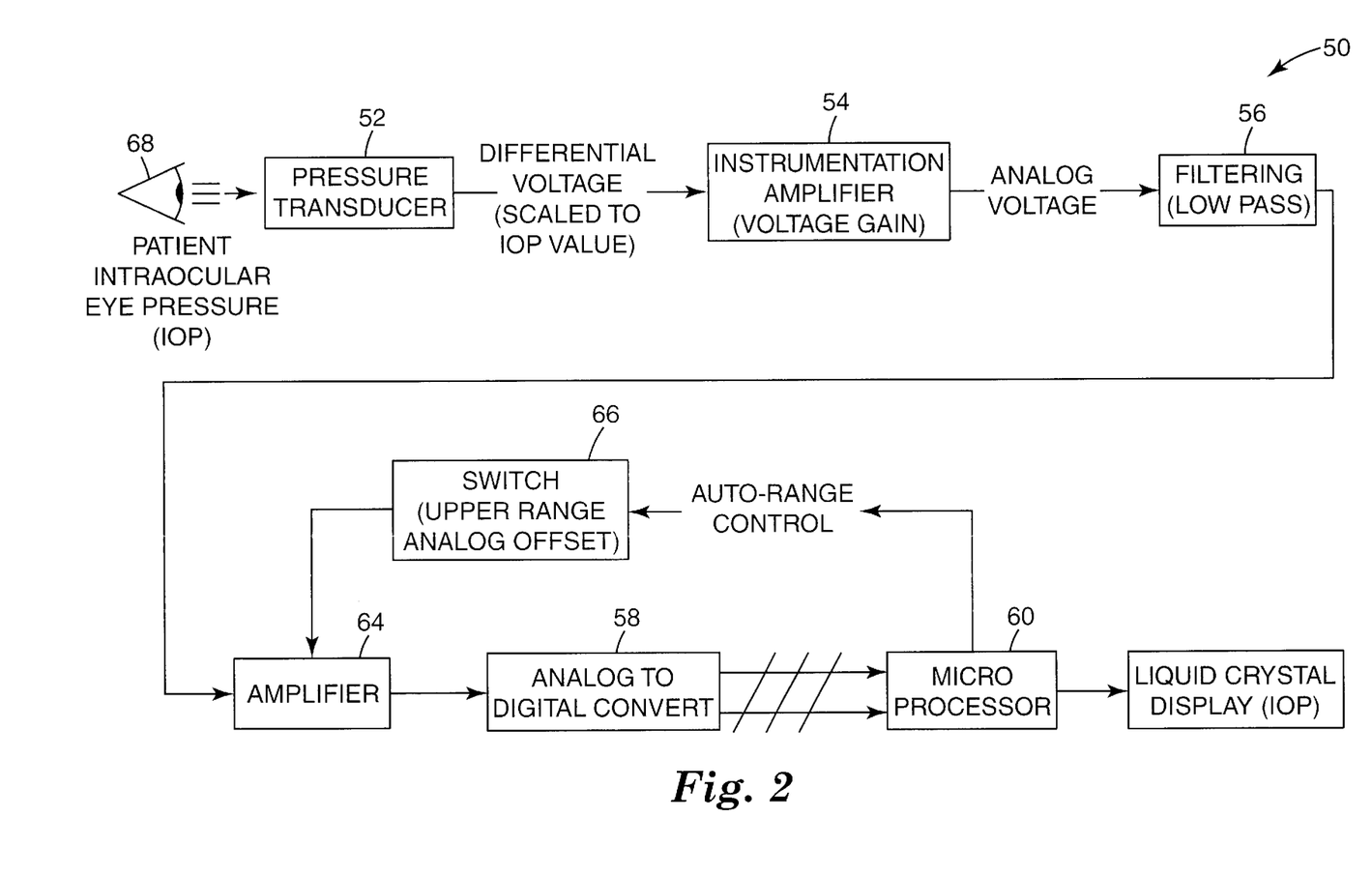
FIG. 2 is a block diagram of a tonometry system useful with the method of FIG. 1.
Figure 3:
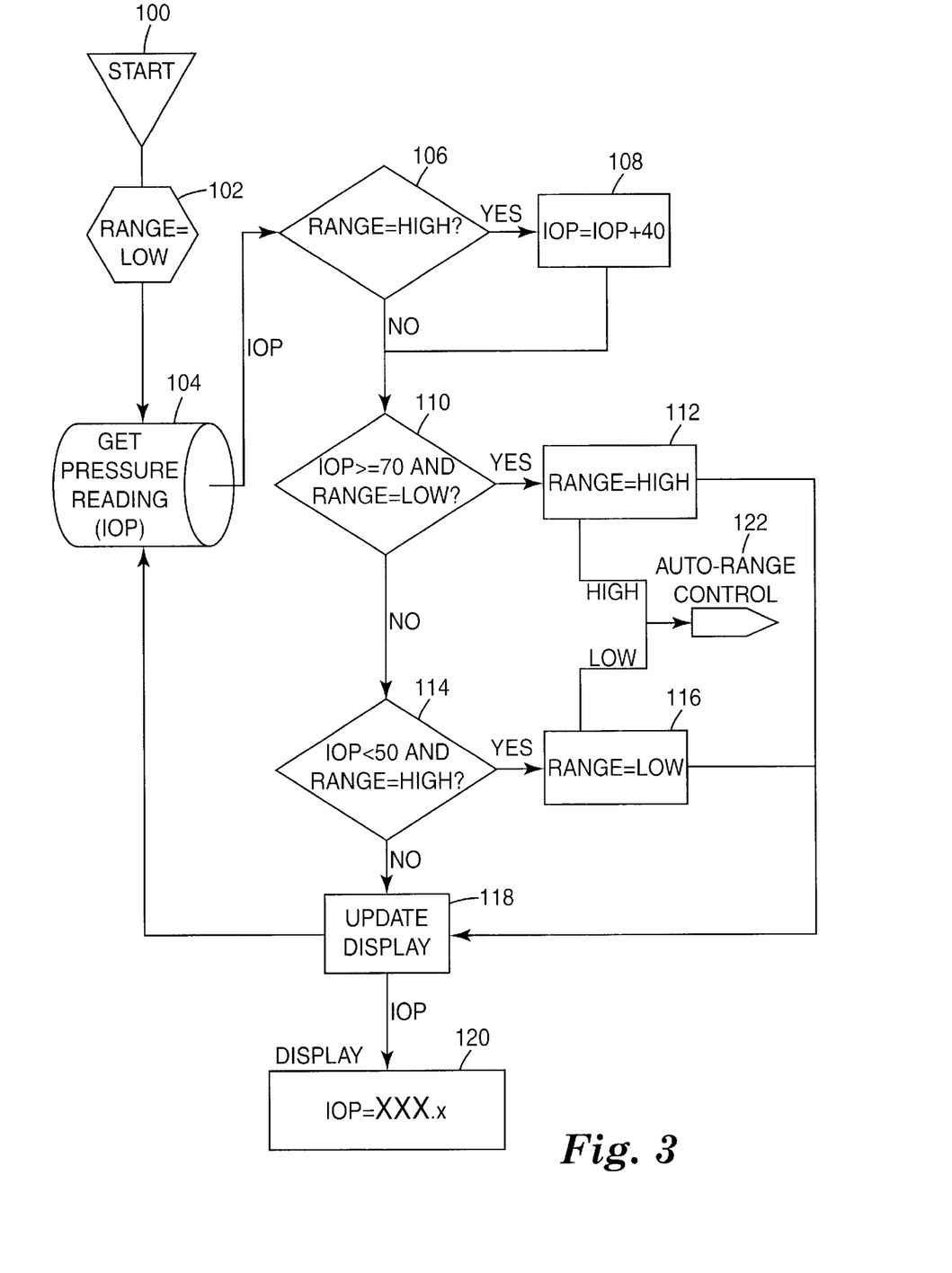
FIG. 3 is a flow diagram illustrating control of the tonometry system of FIG. 2.

A high-pressure range tonometer useful with the method of the present invention can assume a wide variety of forms, but is preferably an applanation or indentation tonometer. In a preferred embodiment, the high-pressure range tonometer is an available pneumatonometer including circuitry and software enhancements that allow the pneumatonometer to provide intraocular pressure measurements up to approximately 120 mm Hg. In this regard, a pneumatonometer produced by Medtronic-Solan (formerly Mentor Ophthalmics) of Jacksonville, Fla., sold under the tradename "Model 30 Classic™" is a highly popular, accurate intraocular pressure measuring instrument. The Model 30 Classic™ device is characterized by a maximum pressure reading of approximately 80 mm Hg, with an accuracy of +/−2 mm Hg. With reference to FIGS. 2 and 3, the available pneumatonometer is preferably modified to provide for the elevated intraocular pressure readings required by the method of the present invention.

Configuration and operation of the Model 30 Classic™ pneumatonometer, along with other available pneumatonometers, is well known. In general terms, the pneumatonometer includes a probe incorporating a pressure transducer that translates backpressure experienced by the probe (otherwise placed in contact with the eye) as a voltage gain or differential voltage. The voltage gain (or back pressure) is indicative of intraocular pressure. The pneumatonometer probe contains a gentle, floating pneumatic sensor that touches the surface of the anesthetized cornea with the exact amount of applanating force required to take a tonometry or tonography measurement.

The sensing element is a lightweight plastic tip covered with a thin, highly elastic silicone membrane. The tip is mounted on a floating piston supported by a porous bearing.

A precisely regulated flow of filtered air enters the piston from the Model 30 Classic pneumatonometer and travels through the end of the sensor tip until it is blocked by the membrane.

When nothing is touching the membrane, air flows to the periphery of the tip, where it escapes through venting ports. However, when the tip touches the eye, the pressure against the membrane causes it to seal the vents, blocking the escape of air and building up pressure in the system. The pressure increases until it matches the IOP and stops when the eye is applanated. At this point, the membrane can no longer maintain the seal and any increased backpressure in the system is released through the venting ports. Applanation is then automatically maintained by the pneumatic feedback system.

A simplified, electrical block diagram for an improved pneumatonometer is provided in FIG. 2, and is referenced generally at 50. Similar to existing pneumatonometers, such as the Model 30 Classic™, the improved pneumatonometer 50 includes a pressure transducer 52, an instrumentation amplifier 54, a filter 56, an A/D converter 58, a microprocessor 60, and a display 62. In addition, the improved pneumatonometer 50 includes an amplifier 64 electrically connected between the filter 56 and the A/D converter 58, as well as a range offset switch 66 electrically connected between the microprocessor 60 and the amplifier 64. As described in greater detail below, the microprocessor 60 is further programmed, such as with software, to effectuate increased intraocular pressure measurement in conjunction with information provided by the switch 66.

Basic pneumatonometer operation is well known in the art, such that only a simplified description is necessary. Basically, the pressure transducer 52 is associated with a probe otherwise contacting the patient's eye 68 (shown generally in FIG. 2). The pressure transducer 50 correlates a sensed voltage gain with a backpressure experience by the probe. This voltage gain or differential voltage is typically in terms of millivolts and is signaled to the instrumentation amplifier 54. The amplifier 54 amplifies the voltage gain to a value in the range of 0–5 volts. The so-amplified differential voltage is signaled to the filter 56. Up to this point, the improved pneumatonometer 50 is identical in construction and processing to available pneumatonometers. Following low pass filtering, the sensed voltage gain is signaled to the amplifier 64 and then to the A/D converter 58. As is known in the art, the A/D converter 58 translates the analog voltage gain to a digital signal that is then provided to the microprocessor 60. As described below, the microprocessor 60 scales the digital voltage gain to an intraocular pressure value, and then evaluates that intraocular pressure value as described below to formulate the measured intraocular pressure. To this end, the microprocessor 60 is programmed to provide auto-range control via the analog offset switch 66 such that intraocular pressure measurements in excess of 80 mm Hg can be provided. Once the microprocessor 60 has ascertained the intraocular pressure, the display 62 is signaled to provide the intraocular information to the surgeon.

As previously described, a currently available pneumatonometer is configured to provide intraocular pressure readings in the range of 0–80 mm Hg. While it might be possible to reconfigure the existing device to include a pressure sensor and/or instrumentation amplifier capable of an increased range of 0–120 mm Hg, retooling and qualification of such a device may be prohibitive. Further, such a redesign would likely sacrifice measurement fidelity (or sensitivity per bit). The improved pneumatonometer 50 overcomes this potential drawback by programming the microprocessor 60 to correlate or scale the sensed voltage differential with either a "low" intraocular pressure range or a "high" intraocular pressure range. As described below, the "low" range is preferably 5–80 mm Hg, and the upper or "high" range is 40–120 mm Hg. In other words, when operating in the "low" range, a nominal or base intraocular pressure value of 5 mm Hg is employed; whereas a nominal or base value of 40 mm Hg is utilized for the "high" range. With this approach, the pressure transducer 52 is identical to existing pneumatonometers, such that the differential voltage or voltage gain is constant, maintaining the highly desirable accuracy of +/−2 mm Hg. With this concept in mind, the microprocessor 60 is programmed to perform an applicable range determination (e.g., either low or high), and then correlate or scale the intraocular pressure measurements accordingly.

With additional reference to FIG. 3, the microprocessor 60 is programmed to begin intraocular pressure range evaluation at step 100. The microprocessor 60 is provided with intraocular pressure range values for both a range setting of "low" and "high". As shown at step 102, the microprocessor 60 initially sets the "range" setting to "low". At step 104, the microprocessor 60 makes an initial determination of the sensed intraocular pressure as previously described, via the sensed voltage gain (or differential voltage) and with reference to the "low" intraocular pressure range.

Steps 106–116 determine whether the designated "range" setting is correct. At step 106, if it is determined that the "range" is set at "high" ("yes" at step 106), the program continues to step 108 at which the measured intraocular pressure (as determined at step 104) is "reset" by adding 40 mm Hg to the intraocular pressure value. With this "new" intraocular pressure value in mind, the program proceeds to step 110. Alternatively, if at step 106 it is determined that the "range" is not set to "high" ("no" at step 106), the program proceeds to step 110.

At step 110, the intraocular pressure value then stored by the microprocessor 60, along with the current range setting are evaluated to determine if the voltage gain or differential voltage has been scaled to the appropriate intraocular pressure range. In particular, a determination is made as to whether the intraocular pressure value is greater than or equal to 70 mm Hg and whether the "range" setting is "low". If, at step 110, it is determined that the intraocular pressure value is greater than or equal to 70 mm Hg and the user entered "range" setting is "low" ("yes" at step 110), the program proceeds to step 112 whereby the microprocessor 60 automatically resets the "range" to "high". With this approach, the program effectively "overrides" an inappropriate range setting of "low". In other words, if the "range" setting is "low", but the measured intraocular pressure is in excess of 70 mm Hg (a value otherwise available in the preferred "low" range), the program determines that the "high" range is more applicable for scaling the voltage gain.

Alternatively, if at step 110, it is determined that the intraocular pressure value is less than 70 mm Hg or that the "range" is set to "low", the program proceeds to step 114, where the intraocular pressure value and the "range" setting are again evaluated. More particular, at step 114, a determination is made as to whether the intraocular pressure value is less than 50 mm Hg and whether the "range" is set at "high". If, at step 114, the intraocular pressure value is less than 50 mm Hg and the "range" setting is "high", the program proceeds to step 116, whereby the range value is automatically reset to "low". Thus, the program effectively "overrides" an inappropriate "range" setting of "high". In other words, if the "range" setting is "high", but the measured intraocular pressure is less than 50 mm Hg (a value otherwise available in the preferred "high" range), the program determines that the "low" range is more applicable for scaling the voltage gain.

Alternatively, if at step 116, it is determined that the intraocular pressure value is greater than 50 mm Hg, or the "range" setting is "high", the program proceeds to step 118 at which the intraocular pressure value is displayed (indicated by the box 120 in FIG. 3).

Returning to step 112 at which the program automatically sets the range value to "high", the microprocessor 60 then utilizes the stored "high" intraocular pressure range to determine intraocular pressure (referenced as "auto-range control" at 122 in FIG. 3). As previously described, in one preferred embodiment, the "high" intraocular pressure range is 40–120 mm Hg. The microprocessor 60 correlates (or scales) the sensed voltage gain or differential voltage with this "high" intraocular pressure range to determine the measured or actual intraocular pressure. The so-measured intraocular pressure is then displayed at step 120 as previously described. Once again, the "high" range affords an intraocular pressure measurement up to 120 mm Hg.

Conversely, returning to step 116, where the program establishes the "range" setting as "low", the microprocessor 60 then correlates (or scales) the sensed voltage gain or differential voltage with the "low" intraocular pressure range to determine the measured intraocular pressure (referenced as "auto-range control" at 122 in FIG. 3). As previously described, in one preferred embodiment, the "low" intraocular pressure range is 5–40 mm Hg. This value is then displayed at step 120.

Finally, following updating of the display at step 120, the program returns to step 104 where the voltage gain, range setting and intraocular pressure measurement are again reviewed by the microprocessor 60 and processed as previously described. As a point of reference, switching of the "range" setting from "low" to "high" for subsequent scaling with the "high" intraocular pressure range is performed by the switch 66 in FIG. 2.

It will be understood that above-described improved pneumatonometer 50 is but one acceptable device for use with the LASIK procedure of the present invention. For example, an existing pneumatonometer can be provided with different programming to provide accurate intraocular pressure measurements in excess of 80 mm Hg (preferably up to or exceeding 120 mm Hg). Even further, a pneumatonometer can be provided with other hardware components capable of providing intraocular pressure readings in excess of 80 mm Hg without requiring different range settings and/or offset values. Even further, a tonometer instrument other than a pneumatonometer can be configured (via hardware and/or software programming) to provide intraocular pressure readings in excess of 80 mm Hg; more preferably in excess of 100 mm Hg; most preferably up to or in excess of 120 mm Hg.

The LASIK method of the present invention provides a marked improvement over previous protocols. In particular, by providing a surgeon with an accurate intraocular pressure measurement following pressure application via the suction ring, uniform microkeratome incisions can be achieved. Unlike existing protocols whereby the surgeon touches the eye with his/her finger to estimate rigidity, the method of the present invention provides the surgeon with reliable intraocular pressure information. In one preferred embodiment, an existing pneumatonometer having an accuracy of +/−2 mm Hg is modified to provide intraocular pressure readings in excess of 80 mm Hg. Regardless, actual measurement of intraocular pressure in excess of 80 mm Hg, more preferably in excess of 100 mm Hg, even more preferably up to or in excess of 120 mm Hg, affords the surgeon valuable information useful for optimally performing the LASIK procedure.

Although the present invention has been described with reference to preferred embodiments, workers skilled in the art will recognize that changes can be made in form and detail without departing from the spirit and the scope of the present invention.

What is claimed:

1. A method of performing a laser-assisted intrastromal in-situ keratomileusis procedure on a patient's eye, the method comprising:
    positioning a suction ring over the eye;
    applying a vacuum pressure to the eye via the suction ring;
    measuring an intraocular pressure of the eye with a high pressure range tonometer;
    determining that the intraocular pressure as measured by the tonometer is greater than 100 mm Hg;
    forming a corneal flap in the eye with a microkeratome;
    retracting the corneal flap;
    ablating a cornea stroma of the eye with a laser; and
    replacing the flap.

2. The method of claim 1, further comprising:
    if the measured intraocular pressure is less than 100 mm Hg, applying additional vacuum pressure to the eye until the measured intraocular pressure is greater than 100 mm Hg.

3. The method of claim 1, further comprising:
    determining whether the measured intraocular pressure is greater than 110 mm Hg.

4. The method of claim 3, further comprising:
    if the measured intraocular pressure is less than 110 mm Hg, applying additional vacuum pressure to the eye until the measured intraocular pressure is greater than 110 mm Hg.

5. The method of claim 1, further comprising:
    determining whether the measured intraocular pressure is not less than 120 mm Hg.

6. The method of claim 1, wherein measuring the intraocular pressure is performed automatically.

7. The method of claim 1, wherein measuring the intraocular pressure includes providing an intraocular eye pressure reading having an accuracy of ±2 mm Hg for intraocular pressures greater than 80 mm Hg.

8. The method of claim 1, wherein the step of determining that the measured intraocular pressure is greater than 100 mm Hg is characterized by the absence of a manual evaluation of intraocular pressure.

9. The method of claim 1, further comprising:
    displaying a measured intraocular pressure greater than 80 mm Hg.

10. The method of claim 1, wherein the high pressure range tonometer is a pneumatonometer.

11. A method of measuring an intraocular pressure in excess of 80 mm Hg as part of a laser-assisted intrastromal in-situ keratomileusis procedure, the method comprising:
    providing a tonometer having a maximum intraocular pressure measuring capability of less than 80 mm Hg;
    applying a vacuum pressure to a patient's eye;
    establishing a range setting for the tonometer;
    receiving an initial intraocular pressure measurement for the eye from the tonometer;
    determining a corrected intraocular pressure measurement based upon the initial intraocular pressure measurement and the range setting; and
    displaying the corrected intraocular pressure measurement;
    wherein the corrected intraocular pressure measurement is greater than 80 mm Hg.

12. The method of claim 11, wherein establishing a range setting includes designating the tonometer as operating in a low-range or a high-range is 40–120 mm Hg.

13. The method of claim 12, wherein the low-range is 5–80 mm Hg, and the high-range is 40–220 mm Hg.

14. The method of claim 11, wherein the range setting is initially manually selected.

15. The method of claim 14, further comprising:
    determining whether the initial intraocular pressure measurement corresponds with the manually selected range setting.

16. The method of claim 15, further comprising:
    resetting the range setting based upon a comparison of the initial intraocular pressure measurement with the manually selected range setting.

17. The method of claim 11, wherein the tonometer is a pneumatonometer.

18. The method of claim 11, wherein determining a corrected intraocular pressure measurement includes increasing the initial intraocular pressure measurement by a predetermined factor.

19. The method of claim 18, wherein the predetermined factor is 40 mm Hg.

20. A system for measuring an intraocular pressure in excess of 80 mm Hg for a patient's eye undergoing a laser-assisted intrastromal in-situ keratomileusis procedure, the system comprising:
- a tonometer capable of measuring a maximum intraocular pressure of less than 80 mm Hg; and
- a processor associated with the tonometer for receiving intraocular pressure measurements from the tonometer, the processor capable of:
  - establishing a range setting for the tonometer,
  - receiving an initial intraocular pressure measurement from the tonometer,
  - determining a corrected intraocular pressure measurement based upon the initial intraocular pressure measurement and the range setting,
  - displaying the corrected intraocular pressure measurement;
- wherein the corrected intraocular pressure measurement is greater than 80 mm Hg.

21. The system of claim 20, wherein establishing a range setting includes designating the tonometer as operating in a low-range or a high-range.

22. The system of claim 20, wherein the range setting is initially manually selected.

23. The system of claim 22, further comprising:
- determining whether the initial intraocular pressure measurement corresponds with the manually selected range setting.

24. The system of claim 23, further comprising:
- resetting the range setting based upon a comparison of the initial intraocular pressure measurement with the manually selected range setting.

25. The system of claim 20, wherein the tonometer is pneumatonometer.

26. The system of claim 20, wherein determining a corrected intraocular pressure measurement includes increasing the initial intraocular pressure by a predetermined factor.

27. The system of claim 26, wherein the predetermined factor is 40 mm Hg.

* * * * *

UNITED STATES PATENT AND TRADEMARK OFFICE
CERTIFICATE OF CORRECTION

PATENT NO. : 6,730,073 B2
DATED : May 4, 2004
INVENTOR(S) : John Bruce

It is certified that error appears in the above-identified patent and that said Letters Patent is hereby corrected as shown below:

Title page,
Item [56], References Cited, FOREIGN PATENT DOCUMENTS, after "6/2002", insert -- A61F/9/013 -- therefor.

Column 10,
Line 51, after "high-range", delete "40-220" and insert -- is 40-120 mm Hg --.

Column 12,
Line 15, after "is", insert -- a --.
Line 19, after "pressure" insert -- measurement -- therefor.

Signed and Sealed this

Twenty-second Day of November, 2005

JON W. DUDAS
*Director of the United States Patent and Trademark Office*